(12) United States Patent
Rose et al.

(10) Patent No.: US 7,081,243 B1
(45) Date of Patent: Jul. 25, 2006

(54) RHABDOVIRUSES WITH REENGINEERED COATS

(75) Inventors: John K. Rose, Guilford, CT (US); Matthias Schnell, Harleysville, PA (US); E. Erik Johnson, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/462,543

(22) PCT Filed: Jul. 10, 1998

(86) PCT No.: PCT/US98/14527

§ 371 (c)(1),
(2), (4) Date: Aug. 25, 2000

(87) PCT Pub. No.: WO99/02657

PCT Pub. Date: Jan. 21, 1999

Related U.S. Application Data

(60) Provisional application No. 60/052,366, filed on Jul. 11, 1997.

(51) Int. Cl.
 *A61K 39/21* (2006.01)
(52) U.S. Cl. .................. 424/199.1; 424/202.1; 424/224.1; 435/320.1
(58) Field of Classification Search .............. 435/69.1, 435/69.7, 320.1; 424/188.1, 199.1, 192.1, 424/208.1, 224.1, 202.1
See application file for complete search history.

(56) References Cited

U.S. PATENT DOCUMENTS

| 5,716,821 A | 2/1998 | Wertz et al. |
| 5,789,229 A | 8/1998 | Wertz et al. |

FOREIGN PATENT DOCUMENTS

| EP | 0702085 A1 | 3/1996 |
| WO | WO 96/34625 | 11/1996 |

OTHER PUBLICATIONS

Schnell, M. J., et al., 1996, "Foreign glycoproteins expressed from recombinant vesicular stomatitis viruses are incorporated efficiently into virus particles.", Proc. Natl. Acad. Sci. USA 93:11359-11365.*

Lawson, N. D., et al., 1995, "Recombinant vesicular stomatitis viruses from DNA", Proc. Natl. Acad. Sci. USA 92:4477-4481.*

(Continued)

*Primary Examiner*—J. S. Parkin
(74) *Attorney, Agent, or Firm*—Jones Day (57) ABSTRACT

Replication-competent recombinant rhabdoviruses that lack a functional glycoprotein gene and express at least one foreign polypeptide such as a celluar receptor for another virus in their viral envelopes are useful in the treatment of pathogenic viruses. In one embodiment, a recombinant vesicular stomatitis virus (VSV) lacking its glycoprotein (G) gene and expressing instead the HIV receptor and a coreceptor is employed in a method for treating persons infected with HIV. The recombinant virus is defective for entry into normal cells but is able to control HIV infection in a T cell line by replicating in, and killing, HIV-infected cells.

9 Claims, 4 Drawing Sheets

OTHER PUBLICATIONS

Feng, Y., et al., 1996, "HIV-1 entry cofactor: functional cDNA cloning of a seven-transmembrane, G protein-coupled receptor.", Science 272(5263):872-7.*

Gait, M. J., and J. Karn, 1995, "Progress in anti-HIV structure-based drug design.", Trends Biotech. 13(10):430-8.*

Yarchoan, R., and S. Broder, 1992, Correlation between the in vitro and in vivo activity of anti-HIV agents: implications for future drug development., J. Enzyme Inhib. 6(1):99-111.*

Maddon, P. J., et al., 1986, "The T4 gene encodes the AIDS virus receptor and is expressed in the immune system and the brain", Cell 47:333-348.*

U.S. Appl. No. 08/435,032, filed May 4, 1995, Rose.

U.S. Appl. No. 08/646,695, filed May 3, 1996, Rose.

Alkhatib et al., 1996, "CC CKR5: a RANTES, MIP-1alpha, MIP-1beta receptor as a fusion cofactor for macrophage-tropic HIV-1", Science, 272(5270):1955-8.

Berson et al., 1996, "A seven-transmembrane domain receptor involved in fusion and entry of T-cell-tropic human immunodeficiency virus type 1 strains", J Virol., 70(9):6288-95.

Choe et al., 1996, "The beta-chemokine receptors CCR3 and CCR5 facilitate infection by primary HIV-1 isolates", Cell, 85(7):1135-48.

Deng et al., 1996, "Identification of a major co-receptor for primary isolates of HIV-1", Nature, 381(6584):661-6.

Doranz et al., 1996, "A dual-tropic primary HIV-1 isolate that uses fusin and the beta-chemokine receptors CKR-5, CKR-3, and CKR-2b as fusion cofactors", Cell 85(7):1149-58.

Doyle and Strominger, 1987, "Interaction between CD4 and class II MHC molecules mediates cell adhesion", Nature, 330(6145):256-9.

Dragic et al., 1996, "HIV-1 entry into CD4+ cells is mediated by the chemokine receptor CC-CKR-5", Nature, 381(6584):667-73.

Feng et al., 1996, "HIV-1 entry cofactor: functional cDNA cloning of a seven-transmembrane, G protein-coupled receptor", Science, 272(5263):872-7.

Florkiewicz and Rose, 1984, "A cell line expressing vesicular stomatitis virus glycoprotein fuses at low pH", Science, 225(4663):721-3.

Fuerst et al., 1986, "Eukaryotic transient-expression system based on recombinant vaccinia virus that synthesizes bacteriophage T7 RNA polymerase", Proc Natl Acad Sci U S A, 83(21):8122-6.

Johnson et al., 1997, "Specific targeting to CD4+ cells of recombinant vesicular stomatitis viruses encoding human immunodeficiency virus envelope proteins", J Virol., 71(7):5060-68.

Knipe et al., 1997, "Maturation of viral proteins in cells infected with temperature-sensitive mutants of vesicular stomatitis virus", J Virol., 21(3):1149-58.

Lapham et al., 1996, "Evidence for cell-surface association between fusin and the CD4-gp120 complex in human cell lines", Science, 274(5287):602-5.

Lawson et al., 1995, "Recombinant vesicular stomatitis viruses from DNA", Proc Natl Acad Sci U S A, 92(10):4477-81.

Maddon et al., 1986, "The T4 gene encodes the AIDS virus receptor and is expressed in the immune system and the brain", Cell, 47(3):333-48.

Mebatsion et al., 1996, Highly stable expression of a foreign gene from rabies virus vectors. Proc Natl Acad Sci U S A, 93(14):7310-4.

Mebatsion et al., 1996, "Budding of rabies virus particles in the absence of the spike glycoprotein", Cell, 84(6):941-51.

Moore J P, 1997, "Coreceptors: implications for HIV pathogenesis and therapy", Science, 276(5309):51-2.

Reed and Muench, 1938, "A simple method of estimating fifty percent endpoints", American Journal of Hygiene 27:493-497.

Reinherz et al., 1979, "Separation of functional subsets of human T cells by a monoclonal antibody", Proc Natl Acad Sci U S A, 76(8):4061-5.

Riedel et al., 1984, "Cell surface expression of fusogenic vesicular stomatitis virus G protein from cloned cDNA", EMBO J., 3(7):1477-83.

Rose et al., 1991, "A new cationic liposome reagent mediating nearly quantitative transfection of animal cells", Biotechniques, 10(4):520-5.

Sattentau and Weiss, 1988, "The CD4 antigen: physiological ligand and HIV receptor", Cell, 52(5):631-3.

Schnell et al., 1996, "Foreign glycoproteins expressed from recombinant vesicular stomatitis viruses are incorporated efficiently into virus particles", Proc Natl Acad Sci U S A., 93(21):11359-65.

Schnell et al., 1996, "The minimal conserved transcription stop-start signal promotes stable expression of a foreign gene in vesicular stomatitis virus", J Virol., 70(4):2318-23.

Schnell et al., 2000, "Recombinant rabies virus as potential live-viral vaccines for HIV-1", Proc Natl Acad Sci U S A, 97(7):3544-9.

Schuitemaker and Miedema, 1996, "Viral and cellular determinants of HIV-1 replication in macrophages", AIDS, 10 Suppl A:S25-32.

Shaw et al., 1989, "The lck tyrosine protein kinase interacts with the cytoplasmic tail of the CD4 glycoprotein through its unique amino-terminal domain", Cell, 59(4):627-36.

Shockett et al., 1995, "A modified tetracycline-regulated system provides autoregulatory, inducible gene expression in cultured cells and transgenic mice", Proc Natl Acad Sci U S A, 92(14):6522-6.

Till et al., 1988, "HIV-infected cells are killed by rCD4-ricin A chain", Science, 25;242(4882):1166-8.

Trkola et al., 1996, "CD4-dependent, antibody-sensitive interactions between HIV-1 and its co-receptor CCR-5", Nature, 384(6605):184-7.

Wagner et al., 1996, "Rhabdoviridae: The viruses and their replication", In Fields Virology, B.N. Fields and D.M. Knipe (eds.), Lippincott-Raven, New York.

Weiss RA., 1993, "How does HIV cause AIDS?", Science, 28;260(5112):1273-9.

Whelan et al., 1995, "Efficient recovery of infectious vesicular stomatitis virus entirely from cDNA clones", Proc Natl Acad Sci U S A, 92(18):8388-92.

Willey et al., 1988, "In vitro mutagenesis identifies a region within the envelope gene of the human immunodeficiency virus that is critical for infectivity", J Virol., 62(1):139-47.

Wu et al., 1996, "CD4-induced interaction of primary HIV-1 gp120 glycoproteins with the chemokine receptor CCR-5", Nature, 384(6605):179-83.

Metabolism et al., 1997, "A CXCR4/CD4 Pseudotype Rhabdovirus That Selectively Infects HIV-1 Envelope Protein-Expressing Cells", Cell, 90:841-47. [Sep. 1997].

Schnell et al., 1997, "Construction of a Novel Virus That Targets HIV-1 Infected Cells and Controls HIV-1 Infection", Cell, 90:849-57. [Sep. 1997].
Schubert et al., 1992, "Insertion of the Human Immunodeficiency Virus CD4 Receptor into the Envelope of Vesicular Stomatitis Virus Particles", Journal of Virology, 66(3):1579-89.

* cited by examiner

RHABDOVIRUSES WITH REENGINEERED COATS

RELATED APPLICATION DATA

This application claims priority benefit of co-pending U.S. application Ser. No. 60/052,366, filed 11 Jul. 1997.

The invention was made with partial government support under NIH grants AI24345 and AI49235. The government has certain rights in the invention.

TECHNICAL FIELD OF THE INVENTION

This invention relates primarily to replication-competent rhabdoviruses which lack a functional glycoprotein gene and express in the viral coat at least one receptor for another virus. Recombinant rhabdoviruses of the invention such as vesicular stomatitis virus which express at least one cellular receptor and a coreceptor of another pathogenic virus such as HIV are useful for the treatment of patients infected with the pathogenic virus.

BACKGROUND OF THE INVENTION

To cause infection, membrane-enveloped viruses such as human immunodeficiency virus type 1 (HIV-1) must first bind receptors at the cell surface and subsequently fuse their own membrane with that of the cell. This fusion process releases the viral genetic material into the cytoplasm and initiates infection. Entry of HIV-1 into cells has long been known to require virus binding to the cell surface molecule CD4 (Maddon, et al., 1986; Sattentau and Weiss, 1988), and recent studies have defined chemokine receptor molecules, CXCR4 (Feng, et al., 1996; Berson, et al., 1996), CCR5 (Alkhatib, et al., 1996; Choe, et al., 1996; Deng, et al., 1996; Doranz, et al., 1996; Dragic, et al., 1996), and CCR3 (Choe, et al., 1996; Doranz, et al., 1996) as co-receptors required for entry. HIV entry occurs in stages: initial binding of the viral envelope protein (designated gp120/41) to CD4 is followed by conformational changes that allow binding to coreceptor and subsequent coalescence of the viral and cellular membranes (Lapham, et al., 1996; Trkola, et al., 1996; Wu, et al., 1996). HIV-infected cells express gp120/41 on the cell surface during infection and prior to its incorporation into budding HIV-1 particles.

Recent studies have shown that vescisular stomatitis virus (VSV) has potential as a high level expression vector capable of incorporating foreign proteins into the viral envelope (Schnell, et al., 1996a; Schnell, et al., 1996b). VSV causes an extremely rapid cytopathic infection in most animal cells including human T cells in culture, but is normally non-pathogenic in humans (for review see Wagner and Rose, 1996). Within two to three hours after infection, VSV blocks host cell protein synthesis and within eight hours produces very large quantities of progeny virus particles that bud from the cell surface prior to cell lysis. VSV has a non-segmented, negative-strand RNA genome that is copied in the cytoplasm of infected cells by the viral RNA polymerase to generate five mRNAs encoding the five structural proteins. Only one of these proteins, a glycoprotein designated G, is present in the viral membrane and is responsible for the very broad host range of VSV. G protein recognizes cell surfaces and catalyzes fusion of the viral membrane with cellular membranes (Florkiewicz and Rose, 1984). Foreign membrane proteins such as CD4 and other viral membrane proteins can be expressed at very high levels from the genome of recombinant VSVs and these molecules are then incorporated at high levels into the viral membrane along with G protein (Schnell, et al., 1996b).

SUMMARY OF THE INVENTION

It is an objective of the invention to utilize this strategy to engineer recombinant viruses that can be employed to target cells infected with another virus such as HIV.

It is a further and more specific objective to provide a method for treating a person infected with HIV.

These and other objectives are accomplished by the present invention, which provides replication-competent recombinant rhabdoviruses such as vesicular stomatitis viruses (VSV) that lack a functional glycoprotein gene and express in their viral coats at least one foreign polypeptide. In preferred embodiments, the foreign polypeptide is a cellular receptor for another virus and is expressed in a manner sufficient to target cells infected with the other virus. In one embodiment, the invention provides replication-competent recombinant vesicular stomatitis virus which lacks a functional G glycoprotein gene and displays at least one cellular receptor for a pathogenic mammalian virus. Where the other virus is HIV, the expressed polypeptide is an HIV receptor such as CD4, an HIV coreceptor such as CXCR4, and/or mixtures of these.

The invention correspondingly provides methods for treating patients infected with a pathogenic virus by administering to the patient an effective amount of a recombinant rhabdovirus of the invention such as VSV which expresses in its viral envelope at least one receptor for the pathogenic virus. As set out hereafter, treatment methods for patients infected with HIV-1 and/or HIV-2 are disclosed.

DESCRIPTION OF THE FIGURES

FIG. 1 illustrates diagrams of recombinant VSV genomes. The order of the genes in wild-type VSV and in the recombinant VSVs described is shown. Each extra gene was inserted so that it contained the appropriate signals specifying VSV polymerase transcription initiation and termination. The details of plasmid constructions and derivation of the recombinant viruses are given in the Examples. The genes are transcribed from left to right from the negative strand RNA genome which is shown in the 3'–5' orientation.

FIG. 2 shows photographs of cultures illustrating that VSVs lacking the G gene form plaques on a complementing cell line. BHK-G cells were seeded on 6-well plates (1.5× $10^5$ cells in each well), and G protein expression was induced by removal of tetracycline. The indicated dilutions of 100 µl the VSVΔG-CD4 virus ($10^{-2}$, $10^{-3}$ and $10^{-4}$) were added 16 h later, followed by addition of 2 ml of DME containing 2% methylcellulose. Cells were incubated for 48 h and then stained with napthalene black to visualize the small plaques. Wild-type VSV plaques are much larger and are visible after 18 h, but plaque formation by the defective virus on this cell line was slower, probably because of the reduced level of complementing VSV G protein expressed.

FIG. 3 shows immunoelectron microscopic visualization of CD4 in the envelopes of VSVΔG-CD4 and VSVΔG-CC4. Purified wild-type VSV, VSVΔG-CD4, or VSVΔG-CC4 particles were negatively stained with phosphotungstic acid after labeling with a monoclonal antibody directed to CD4 followed by gold-conjugate goat anti-mouse IgG particles. Wild-type VSV particles contained visible spikes of VSV G protein trimers (arrows) and did not bind antibody to CD4 (wild-type VSV, left panel), while VSVΔG-CD4 or VSVΔG-CC4 bound anti-CD4 antibody and did not show visible spikes on the surface.

FIG. 4 illustrates analysis of HIV-1 and VSVΔG-CC4 infection by immunofluorescence microscopy. Duplicate cultures of Jurkat cells were infected with HIV-1 strain IIIB and five days later, superinfected with VSVΔG-CC4 (panel D, E, F) or propagated without superinfection (panel A, B, C). Jurkat cells that were uninfected with HIV-1 were also infected with VSVΔG-CC4 (panel G, H, I). Fourteen days after the VSVΔG-CC4 infection, cells were fixed and labeled with a mouse monoclonal antibody to VSV N protein and a secondary, affinity-purified, rhodamine-conjugated anti-mouse antibody (detected in panels C, F, I) and with a human polyclonal anti-HIV immune globulin followed by affinity-purified, FITC-conjugated anti-human antibodies (detected in panels B, E, H). Panels A, D, and G show Nomarski images of the same fields of cells shown stained in the two images to their right.

FIG. 5 provides line graphs illustrating quantitation of HIV-1 and VSVΔG-CC4 infection in Jurkat cells. Duplicate cultures of Jurkat cells were infected with HIV-1 IIIB at day 0 and either superinfected with VSVΔ-CC4 five days later (■) or propagated without superinfection (□). The percentage of HIV+ cells was determined by immunofluorescence microscopy on the days indicated (FIG. 5A). The percentage of HIV+ cells that were also infected with VSVΔG-CC4 was determined by immunofluorescence microscopy to detect VSV N protein (FIG. 5B). One hundred to two hundred cells were counted from multiple random fields to determine the percentages of cells staining positive for HIV or VSV antigens.

FIG. 6 provides line graphs illustrating the effect of VSVΔG-CC4 infection on production of infectious HIV-1 and on release of RT. Media from Jurkat cell cultures were analyzed for infectious HIV titers and for RT activity as described in the Examples. Titers (FIG. 5A) were performed in triplicate and are reported as $TCID_{50}$/ml (□, HIV infected only; ■, HIV+VSVΔG-CC4). Titers determined by this assay were consistent with titers determined by an indirect immunofluorescence assay detecting HIV antigens. RT activity (FIG. 5B) is reported in total counts per minute (cpm) bound to the DEAE paper after subtraction of a backgrounds of less than 50 cpm (□, HIV infected only; ■, HIV+VSVΔG-CC4; Δ, VSVΔG-CC4 infected only). The numbers plotted are the average of duplicates that agreed within 5%. Samples were collected from Jurkat cultures on the indicated days after superinfection with VSVΔG-CC4.

DETAILED DESCRIPTION OF THE INVENTION

This invention is based upon the construction of a new virus from vesicular stomatitis virus (VSV) that is replication-competent and kills cells rapidly, but is only able to infect cells that are first infected with HIV. The virus contains a deletion in the VSV envelope glycoprotein gene and expresses instead the genes for the HIV receptor CD4 and an HIV coreceptor, CXCR4. The virus kills HIV-infected cells in culture and controls HIV infection.

In the practice of this invention, replication-competent recombinant rhabdoviruses are generated which lack a functional glycoprotein gene and express a foreign polypeptide in their viral envelopes. By "foreign" is meant not naturally occurring in the rhabdovirus transformed. The foreign polypeptide is one that binds to a mammalian cell such as a cellular receptor and/or coreceptor for another virus in many embodiments, and an antibody in other embodiments. The invention is particularly suited to target cells infected with membrane-enveloped viruses. The invention provides a general strategy of virus targeting to infected cells in cases where receptor(s) recognized by viral envelope proteins are known, and the viral protein has membrane fusion activity. Likewise, both conventional and hybrid antibodies to pathologic cells are also known and are used to target these cells. In either case, foreign polypeptides are expressed in the rhabdovirus in a manner sufficient to target cells to be killed. Therefore, as used herein, by a "recombinant rhabdovirus lacking a functional glycoprotein gene" is meant a virus having any alteration or disruption of the glycoprotein gene, and/or expressing a poorly functional or nonfunctional glycoprotein, or combinations thereof.

In the examples that follow, recombinant VSVs are generated which lack a functional envelope glycoprotein G or corresponding gene and express instead at least one receptor or coreceptor of an HIV virus. In preferred embodiments, the G gene is deleted, but any mutation of the gene that alters the host range specificity of VSV or otherwise eliminates the function of the G protein can be employed.

A gene for a foreign polypeptide such as one that binds to mammalian cells infected with a pathogenic virus is then inserted and/or added to the genome of the recombinant rhabdovirus. As summarized above, in many typical embodiments, the added gene is a receptor recognized by a virus glycoprotein and that is present on the surface of mammalian cells. However, recombinant rhabdoviruses engineered to kill other cells, e.g., cancer cells, are encompassed by the invention. In these embodiments, genes for specific antibodies and a membrane fusion protein are typically incorporated into rhabdoviruses lacking the a functional glycoprotein gene.

The invention thus provides medical or veterinary methods for treating a patient (human being or animal) infected with a pathogenic mammalian virus by administration to the patient of an effective amount of a replication-competent recombinant vesicular stomatitis virus which lacks a functional G glycoprotein gene and displays a receptor of the pathogenic virus in its coat in a manner sufficient to target cells infected with the pathogenic virus. An example wherein the pathogenic, membrane-enveloped virus is HIV and the envelope proteins added to the VSV are an HIV receptor and a specific coreceptor is given in the Examples section hereafter. In that illustration, a T cell tropic HIV is employed, but recombinant VSVs of the invention can been engineered to express coreceptors of other HIV strains. Other embodiments express a receptor and not a coreceptor, and some recombinant VSVs of the invention express more than one HIV coreceptor.

In the practice of a preferred embodiment of the invention, a patient infected with HIV is treated by administering to the patient an effective amount of a replication-competent recombinant vesicular stomatitis virus which lacks a functional glycoprotein G gene and expresses at least one HIV receptor such as CD4 and at least one HIV coreceptor such as CXCR4, CCR5, CCR3, and/or mixtures thereof. An exemplary construct is VSVΔG-CC4 described hereafter and illustrated in FIG. 1.

Administration of a recombinant rhabdovirus of the invention to a person or other mammal can be via any local or systemic method known by skilled workers, but is preferably systemic. Systemic administration includes intravenous, intramuscular, or intradermal administration by sterile injections, parenteral administration, and the like, typically in combination with a pharmaceutically acceptable carrier and/or other adjuvant or adjunct compound that maintains viability of the recombinant VSV virus or other rhabdovirus, or enhances its effect. Combinations of therapies may also be employed.

The amount of recombinant rhabdovirus necessary to bring about therapeutic treatment is not fixed per se, and necessarily depends upon the severity or the extent of disease. Administration is facilitated and, in some cases additional therapeutic effects are provided by, the carrier. When a carrier is employed, it is necessary that it be inert in the sense of not inactivating the recombinant VSV or other rhabdovirus and in the sense of not bringing about any adverse effect to the patient to which it is administered. In most situations, doses are dependent upon the extent of the patient's disease, the age, weight, and clinical condition of the patient to be treated, the potency of the recombinant virus, the adjuvants or adjunct compounds (if any) employed, and the concentrations of recombinant rhabdovirus and other ingredients which are typically put together in association with a pharmaceutically acceptable carrier. Most preferably, administration of the recombinant rhabdoviruses of the invention reduces the diseased cells in the patient so signficantly that they are barely detectable or undetable.

It is an advantage of the invention that preferred recombinant VSVs which incorporate the receptor of one virus in the coat of another kill cells infected with the other virus rapidly and thus control infection. It is a further advantage of the invention that recombinant VSVs or other rhabdoviruses of the invention are genetically engineered to specific targets, and kill only infected or pathogenic cells.

The following examples are presented to further illustrate and explain the present invention and should not be taken as limiting in any regard.

EXAMPLES

In the studies reported herein VSV recombinants are generated which exhibit a complete deletion of the VSV G gene and a substitution instead of the genes for CD4 and CXCR4. These viruses assemble particles containing both CD4 and CXCR4 in their envelopes and are targeted specifically to infect HIV-1-infected cells.

Experimental Procedures

Plasmid construction. Digestion with MluI and SphI was used to delete the entire VSV G gene from pVSV-CD4 (Schnell et al., 1996b). The resulting plasmid was designated pVSVΔG-CD4. A plasmid encoding the CXCR4 protein with an HA epitope tag was described previously (Berson et al., 1996). CXCR4 was amplified by PCR from this plasmid with VENT polymerase (Stratagene) using primers 5'-ACTGCCCGGGCTCGAGGTTACCATGGAGGGGATCAG-3' (SEQ ID NO: 1) and 5'-AGCTGCGGCCGCTAGCTTAGCTCCCGGGAAGAGATGCG-3' (SEQ ID NO: 2). The first primer contains an XhoI site and the second an NheI site (boldface letters). The PCR product was digested with XhoI and NheI and cloned into pVSV-XN1 (Schnell et al., 1996a) that was digested with XhoI and NheI. The resulting plasmid was designated pVSV-CXCR4. The G gene was deleted from pVSV-CXCR4 with XhoI and MluI. The coding sequence for human CD4 was amplified from pCD4 (Shaw et al., 1989) by PCR using primers 5'-CCGGGTACCACGCGTACAATGAACCGGGGAGTCCCTTTTAG-3' (SEQ ID NO: 3) and 5'-GGGCCCCTCGAGCGTGATATCTGTTAGTTTTTTTCATACTCAAATGGGGCTACATGTCTTC-3' (SEQ ID NO: 4). The first primer contains an MluI site (boldface letters); the second primer contains an XhoI site (boldface letters) and a VSV transcription stop-start signal (underlined letters). The CD4 gene was inserted at the site of the G deletion to generate a plasmid that was designated pVSVΔDG-CC4.

Construction of a BHK cell line expressing VSV G protein. The tetracycline-regulated system employed was described previously (Shockett et al., 1995). A VSV G gene was prepared from a plasmid designated pBSG by digestion with XhoI. Extensions were filled in with Klenow enzyme, and the fragment ligated to pTet-Splice (Life Technologies) that had been cleaved with EcoRV. The resulting plasmid was called pTET-G. BHK cells on 10 cm plates (20% confluent) were transfected with 1 µg pTET-G and 10 µg pTet-TAk (Life Technologies) using the CaPO$_4$ method (mammalian transfection kit; Stratagene). One day after transfection 0.5 µg/ml tetracycline was added to suppress G protein expression, which is toxic to BHK cells, and stable transfected cells were selected by adding 0.75 mg/ml geneticin (G418). Ten days after transfection, cell colonies were isolated and, after induction by removal of tetracycline, they were screened for expression of VSV G protein by immunofluorescence microscopy.

Recovery of VSV recombinants. Baby hamster kidney cells (BHK-21, ATCC) were maintained in DMEM (Dulbecco's modified Eagle's medium) supplemented with 5% fetal bovine serum (FBS). Cells on 10 cm dishes (~80% confluent) were infected at an MOI of 10 with vTF7-3 (Lawson et al., 1995). After 1 hour, plasmids encoding the N, P, G, and L proteins and the appropriate recombinant anti-genome RNA were transfected into the cells using a cationic liposome reagent containing dimethyldioctadecyl ammonium bromide and phosphatidylethanolamine (Lawson et al., 1995; Rose et al., 1991). Plasmid amounts were 10 µg of the respective full length plasmid (VSVΔG-CD4 or VSVΔG-CC4), 3 µg pBS-N, 5 µg pBS-P, 4 µg BS-G and 2 µg pBS-L. Supernatants of recoveries were filtered through 0.22 µm filters, and 5 ml was used to infect BHK-G cells on 10 cm plates which had been induced for twelve hours by removal of tetracycline. Supernatants of the first passage were filtered twice through a syringe filter (0.1 µm pore size) to remove any vaccinia virus and the viruses were then passaged on 4×10$^6$ BHK-G cells. Supernatants (10 ml) were titered on BHK-G cells and frozen at −80° C. For production of virus stocks, 2×10$^6$ BHK cells on 10 cm plates were infected for 2 h with 10 ml supernatants of VSVΔG-CD4 or VSVΔG-CC4 grown on BHK-G cells, washed three times with phosphate buffered saline (PBS) followed by addition of 10 ml RPMI medium with 10% fetal bovine serum (FBS) or 10 ml DMEM with 5% FBS. At 16 h after infection, supernatants were clarified by centrifugation and used for experiments or stored at −80° C.

Preparation and analysis of viruses. For isolation of virions, a monolayer of BHK cells (~80% confluent) on a 10 cm dish was infected with VSVΔG-CD4 or VSVΔG-CC4 (multiplicity of infection, MOI=5), or wild-type VSV (MOI=0.01). At 16 h after infection, cell debris and nuclei were removed by centrifugation at 1,250× g for 5 min and virus was then purified twice by ultra-centrifugation at 120,000 g through a 20% sucrose solution containing 10 mM Tris-HCl, pH 7.5, and 1 mM EDTA. Virus pellets were resuspended and analyzed by SDS-PAGE (10% acrylamide). Gels were either stained with Coomassie brilliant blue or transferred to nitrocellulose membranes. Membranes were blocked with 5% low fat milk powder in TBST (10 mM Tris-HCl pH 8.0, 150 mM NaCl, 0.05% Tween™-20) for 1 h at room temperature and then incubated with an anti-body directed against CD4 (sheep α-CD4, AIDS Research Reference and Reagent Program) or an antibody 12CA5 (Boehringer-Mannheim) directed against the HA epitope in CXCR4. Proteins were visualized after incubation with horseradish peroxidase-conjugated donkey anti-sheep IgG or horseradish-peroxidase conjugated goat anti-mouse IgG (Jackson Reasearch) for 1 h at room temperature using enhanced chemiluminescence (ECL; Amersham) system.

Electron microscopy and labeling with gold-conjugated antibodies. Virus particles from infection of approximately $10^7$ cells on a 15 cm dish were recovered from the culture medium by first pelleting cell debris at 1,500× g for 10 min. The virus was then concentrated and purified by centrifugation as described above. Virus samples were absorbed onto carbon coated grids for 5 min and then blocked with 1% BSA in PBS for 10 min at room temperature. The grids were then placed on a 50 µl drop of anti-CD4 Mab OKT4 (Reinherz et al., 1979) diluted 1:50 in PBS containing 1% BSA. After 1 hour, excess antibody was removed by placing grids sequentially onto five 50-µl drops of 1% BSA in PBS for 2 min each time. The grids were then placed on a 50-µl drop of goat anti-mouse IgG (Fc) labeled with 15 nm gold particles (AuroProbe, Amersham Inc.). Unbound gold conjugates were removed by five sequential 2-min washes with PBS. The virus-immunogold complexes were then negative stained by incubation the grids for 4 min on 50-µl drops of 2% phosphotungstic acid (ph 7.2). Excess stain was removed and the grids were air dried. Images of viruses were obtained with a Zeiss EM910 electron microscope.

Infection and immunofluorescence microscopy of infected Jurkat cells. Approximately 3×10$^6$ Jurkat Cells (clone E6-1, ATCC #TIB-125) were seeded in T-25 flasks and grown in RPMI medium supplemented with 10% FBS. Infection with HIV-1 strain IIIB was at an MOI of approximately 0.01. At five days post-infection, cells were superinfected with 5 ml of medium containing VSVΔG-CC4. As controls, one HIV-infected culture was not superinfected, and a third culture was infected only with VSVΔG-CC4. Cells were collected for analysis at each time point as follows. One half of the volume of the culture was collected and an equal volume of RPMI supplemented with 10% FBS was added back to the original cultures. Cells were pelleted at 1000 rpm for five minutes at 5° C. in an IEC Centra-7R refridgerated centrifuge (Fisher Scientific). The media was discarded, cells were washed once in 5 ml PBS, and pelleted again. The PBS was removed and cells were resuspended in 100 µl PBS. The cells were then fixed in 1 ml of 3% paraformaldehyde for one hour at room temperature, or overnight at 4° C. After permeabilization in 1% Triton X-100, cells were stained with a monoclonal antibody to VSV N protein and with human polyclonal HIV immunoglobulin (AIDS Research Reference and Reagent Program), followed by rhodamine-conjugated anti-mouse and FITC-conjugated anti-human antibodies (Jackson Research).

Cells were examined and photographed with 40× planapochromat objective on a Nikon Microphot-FX microscope equipped for epifluorescence. Infection of cells with HIV-1 or VSVΔG-CC4 was monitored by counting at least three random fields of cells that typically contained 100–200 cells. Syncytia were counted as single cells.

Determination of HIV Titers. HIV titers were obtained using supernatants from infected cultures and making serial three-fold dilutions in 96-well plates. Ten thousand MT-2 cells provided by the AIDS Research Reference and Reagent Program (ARRRP) were added to each well and the virus and cells were mixed by pipeting. Plates were incubated at 37° C. for 3–5 days and scored for the presence of syncytia. Titers at each time point were performed in triplicate and two or more syncytia per well were counted as positive for HIV infection. Titers were calculated as described previously (Reed and Muench, 1938) and are reported as 50% tissue culture infectious doses (TCID$_{50}$) per ml.

Reverse Transcriptase Assays. Each assay was performed in 96-well plates in duplicate (Willey et al., 1988). Twenty-five microliters of reverse transcription reaction mix (0.05% NP-40, 50 mM Tris-HCl, pH 7.8, 75 mM KCl, 2 mM DTT, 5 mM MgCl$_2$, 5 units oligo (dT)12–18, 5 mg/ml poly A) was added, followed by addition of 10 µl of cell-free culture supernatants. An additional 25 µl of reaction mix was added containing 10 µCi/ml α-[$^{32}$P]-dTTP, and the reaction was placed at 37° C. for 90 minutes. Five microliters of each sample was then spotted onto Whatman DE81 paper, which was allowed to air dry. The DE81 paper was then washed in 2× SSC (0.3 M NaCl, 20 mM sodium citrate) buffer four times, each time at room temperature for five minutes, followed by two one-minute washes in 95% ethanol at room temperature. After air drying, the paper was exposed to a Molecular Dynamics PhosporImager screen overnight. Samples were quantitated directly on the phosphorimager and by counting in a scintillation spectrometer after excision from the paper. Duplicate samples agreed within 5%.

Neutralization of infection by VSVDG-CC4. Polyclonal sheep anti-CD4 serum and anti-gp120 serum (ARRRP) were heat treated at 56° C. for one hour to inactivate complement. The anti-VSV neutralizing monoclonal antibody (II) was a mouse ascites fluid. Neutralizations were performed as follows. VSVΔG-CC4 virus (1 ml derived from ~10$^6$ infected BHK cells) was mixed with 100 µl anti-CD4 or 100 µl anti-VSV for one hour at 37° C., and then the mixture was added to ·10$^6$ Jurkat cells that had been infected with an MOI of 0.01 HIV-1 IIIB five days previously. Alternatively, 100 µl anti-gp120 serum was added directly to 1 ml of HIV-infected Jurkat cells for one hour at 37° C. Then 1 ml of VSVΔG-CC4 was added to the cells. After 3 days, cells were pelleted at 1000 rpm in a clinical centrifuge for 5 minutes and washed once in PBS. Cells were fixed and stained to detect HIV and VSV N protein antigens.

Results

Recovery of VSV recombinants expressing CD4 and CXCR4. Genetic engineering of non-segmented negative-strand RNA viruses such as VSV is complicated by the fact that the minimal infectious unit of the virus is not RNA, but rather the viral RNA genome in a ribonucleoprotein complex composed of nucleocapsid (N) and polymerase proteins (L and P). Infectious VSV can be recovered from plasmid DNA as follows. Four separate plasmids expressing the full-length antigenomic VSV RNA and the N, P and L genes under control of bacteriophage 17 promoters are transfected into cells already infected with a vaccinia virus recombinant expressing T7 RNA polymerase (vTF7-3). Intracellular assembly of the antigenomic RNA into nucleocapsids is followed by VSV replication and transcription to generate infectious, replication-competent VSV (Fuerst et al., 1986; Lawson et al., 1995; Whelan et al., 1995). Additional genes can be expressed from extra transcription units introduced into the VSV genome (Schnell et al., 1996a).

Figure 1:
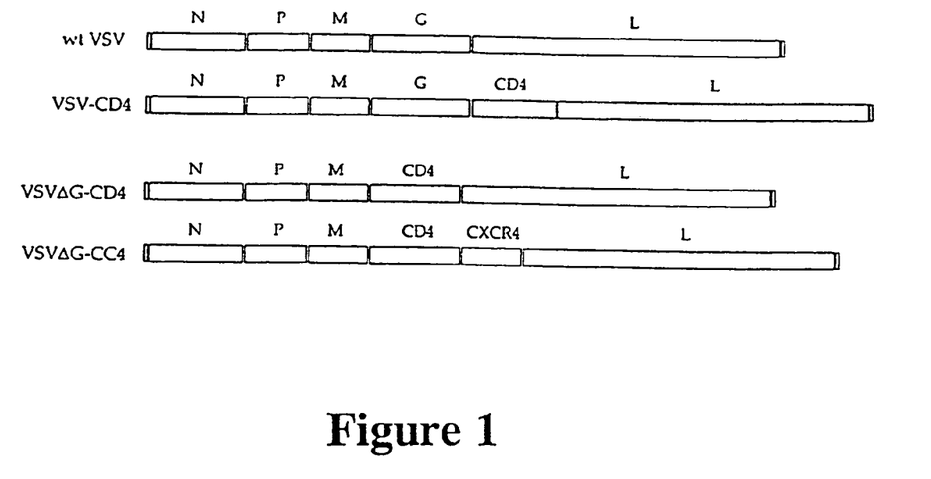

The construction of a VSV recombinant expressing the CD4 protein in addition to the five VSV proteins N, P, M, G and L has been previously reported (Schnell et al., 1996b). To generate a recombinant expressing CD4 and CXCR4 instead of VSV G, the upstream VSV G gene was deleted from the VSVCD4 construct (FIG. 1). The recovery of virus, designated VSVΔG-CD4, was then accomplished by including a complementing plasmid encoding VSV G protein in addition to those encoding N, P, and L. The gene encoding CXCR4 at the position downstream of CD4 was next added and the virus designated VSVΔG-CC4 was recovered. Because the recovered viruses are capable of only a single round of infection on BHK cells, they were initially recovered and grown on cells infected with a vaccinia virus encoding the T7 RNA polymerase and transiently expressing a complementing VSV G protein from a transfected plasmid DNA.

Figure 2:
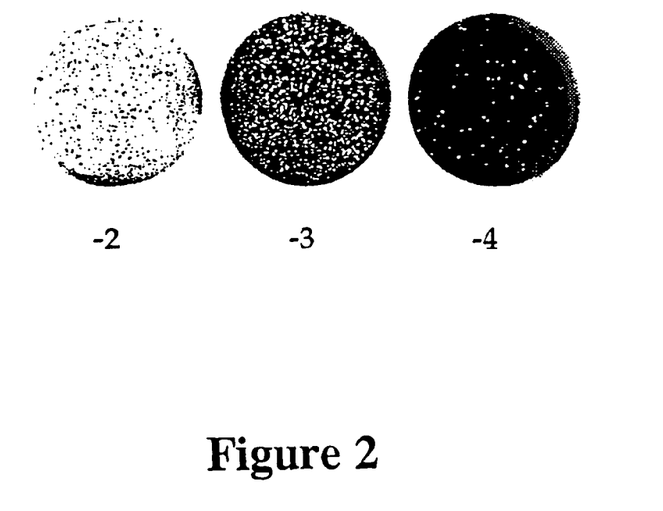

A cell line expressing VSV G protein allows growth of the defective viruses. In order to grow the VSVΔG-CD4 and VSVΔG-CC4 virus in the absence of vaccinia virus, a BHK cell line expressing the VSV G protein from an inducible promoter (Shockett et al., 1995) was generated. FIG. 2 shows that the VSVΔG-CC4 virus forms plaques on this cell line indicating multiple rounds of infection. Titers obtained after growing the defective viruses on this line were in the range of $0.5–1\times10^6$ pfu/ml. These titers are reduced at least 1000-fold compared to those of wild-type VSV presumably because the levels of G protein provided by the complementing cell line are low compared to those expressed in wild-type infection.

Incorporation of CD4 and CXCR4 into the recombinant viruses. To determine if the CD4 and CXCR4 molecules were expressed from the defective viruses and incorporated into virus particles, BHK cells (not expressing VSV G) were infected with VSVΔG-CD4 or VSVΔG-CC4 that had been grown on the BHK-G line (MOI 5). After 16 hours when all cells had been killed, the virus particles were purified from the medium. Viral proteins were then separated by SDS-PAGE and detected by staining with Coomassie blue. The wild-type virus contains the L, G, N, and M proteins (P is a minor protein comigrating with N) while the VSVΔG-CD4 and VSVΔG-CC4 viruses lack G but contain a new protein of about 55,000 daltons, the size expected for CD4. The presence of CD4 in the particles was also verified by western blotting with sheep anti-CD4 antibody or monoclonal antibody 12CA5 to the HA epitope tage in CXCR4. The CXCR4 protein was not detected in VSVΔG-CC4 by staining, perhaps because it contains seven membrane spanning segments that does not bind the stain, but was easily detected by western blotting.

Budding of VSV in the absence of VSV G protein is known to be approximately 20-fold less efficient than budding in its presence (Knipe et al., 1977). Similar results have been obtained for rabies virus (Mebatsion et al., 1996). Although the amounts of protein detected by Coomassie blue staining appeared similar for all viruses, the virus loaded in test lanes were derived from 10' infected BHK cells, while the wild-type virus in the control lane was from only $2\times10^5$, or 50-fold fewer infected cells to achieve similar staining. The results not only confirm the importance of VSV G protein in driving highly efficient virus budding, but also illustrate that significant amounts of virus production occur even in the absence of VSV G protein.

Figure 3:
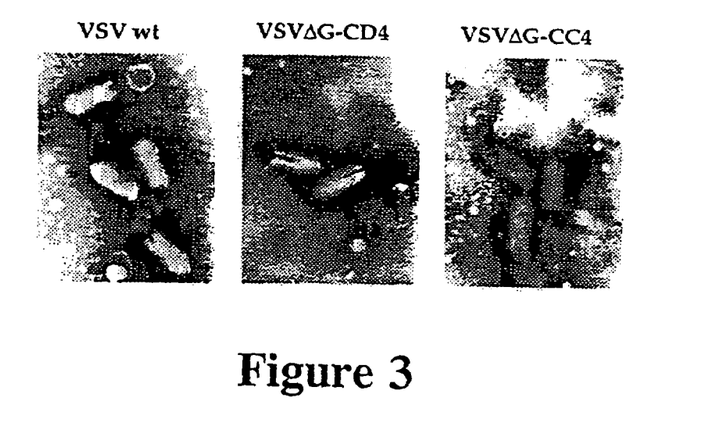

To examine the morphology of the recombinant virus particles and to verify that CD4 was exposed on the viral membrane, purified virus particles were examined by electron microscopy after labeling with antibody to CD4 and a gold-conjugated secondary antibody. Photographs of negatively stained virus particles are shown in FIG. 3. Wild-type VSV particles contained visible G protein spikes (arrows) and did not bind antibody to CD4, while the VSVΔG-CD4 or VSVΔG-CC4 viruses lacked visible spikes and did bind anti-CD4 antibodies. The antibody to CXCR4 used in western blotting recognizes the internal C-terminal HA tag on CXCR4 and therefore is not suitable for labeling virus particles.

Infection of HIV-1 Infected Cells by VSVΔG-CC4. Because cells infected with HIV-1 have the gp120/41 envelope protein on their surface, it might be possible to infect these cells with VSVΔG-CC4. The gp120/41 molecules present on the cell surface should bind to CD4 and CXCR4 on the virus surface and promote fusion of the viral and cell membranes. To test this possibility, a human T cell line (Jurkat) was infected with HIV-1 IIIB. At five days post-infection, it was expected from previous experiments that about half of the cells would be infected with HIV-1, and VSVΔG-CC4 virus was added. Two control cultures, one infected with HIV-1 only, and another infected with VSVΔG-CC4 only, were followed in parallel.

Figure 4:
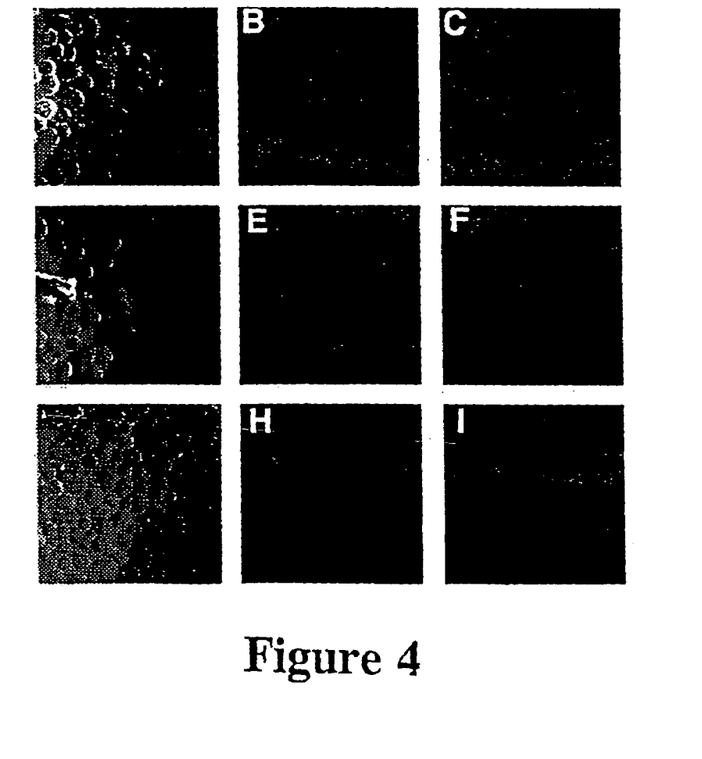

Initially infection by HIV-1 and VSVΔG-CC4 using indirect immunofluorescence microscopy to detect both HIV-1 proteins and VSV nucleocapsid (N) protein was followed. An example of results from the immunofluorescence analysis at 19 days after HIV infection is shown in FIG. 4, along with a Nomarski image of the same field of cells. A compilation of the immunofluorescence data obtained throughout the experiment is graphed in FIG. 5. The fields shown in FIG. 4 illustrate that in the control culture infected with HIV-1 only, nearly all cells stained positive for HIV antigens (A and B) while none of the cells stained positive for VSV N protein (C). In the cells infected with HIV-1 and VSVΔG-CC4, only a small fraction of the cells were positive for HIV-1 antigens (D and E), and the majority of those cells were also positive for VSV N protein (F), indicating that they had been superinfected with VSVΔG-CC4. It was also noted that rare cells that were strongly positive for VSV N protein expression, had only little or no HIV protein evident. These cells may result from shut-off of cellular and HIV protein synthesis by VSVΔG-CC4 or from other mechanisms of infection (see Discussion below). In Jurkat cells infected with VSVΔG-CC4 only, none of the cells showed the presence HIV or VSV N antigens (H, I, and J).

Figure 5A:
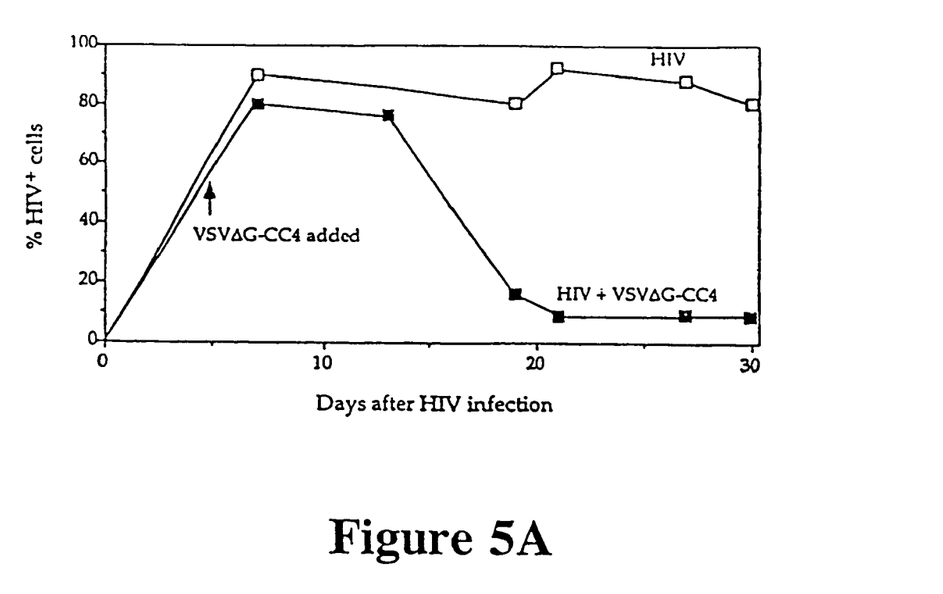
Figure 5B:
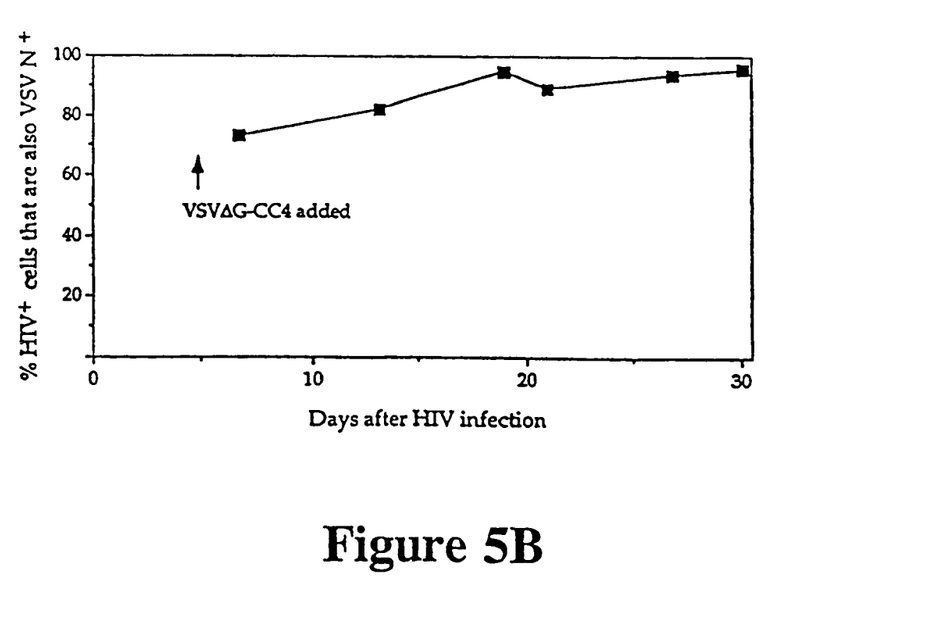

From the quantitation in FIG. 5 it is evident that when cells were infected with HIV-1 alone, the percentage of HIV-1+cells rose to nearly 100% and remained high throughout the experiment. When cells were first infected with HIV-1 and subsequently infected with VSVΔG-CC4, the percentage of $HIV^+$ cells began to decrease at day 14 and plateaued at day 21 to levels between 5 and 10% $HIV^+$. In addition, FIG. 5 shows that the percentage of HIV-$1_+$ cells that were also infected with VSVΔG-CC4 increased and then reached a plateau at around 90–95%. It therefore appears that cells infected with HIV-1 are rapidly superinfected with VSVΔG-CC4 and killed before high levels of HIV-1 can be released. A balance is then reached between the two viruses where HIV infection is controlled by VSVΔG-CC4 infection and maintained at low levels. Very similar results were obtained in an experiment performed with the H9 T cell line, another cell line in which HIV-1 IIIB grows well.

The possibility that the VSVΔG-CD4 virus lacking the coreceptor gene might infect HIV-1 infected cells was also tested. In one experiment it was observed that a low level of infection by VSVΔG-CD4 (about 10% that observed with VSVΔG-CC4) occurred. However, the initial infection could be completely neutralized with antibody to VSV G, indicating that a trace of G protein sufficient to start infection must have been present in the virions. This G protein was presumably carried into the BHK cell line from the input virus grown in the BHK-G line and then incorporated into exiting virions. Interestingly, once the infection was established in HIV-infected Jurkat cells, it persisted for several weeks, indicating that the virus could propagate without encoding its own coreceptor. Presumably budding virions can pick up cell-encoded coreceptor and are then able to propagate. However, control of HIV-1 infection was not as strong as with VSVΔG-CC4, indicating that it is preferable to have the virus encode high levels of the coreceptor. Because the control of HIV infection was less effective without coreceptor, further studies with this virus were not pursued.

Figure 6A:
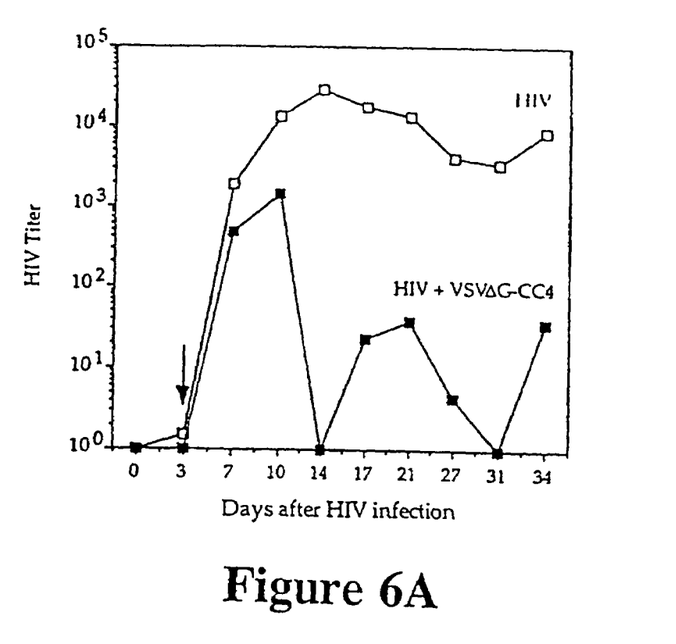
Figure 6B:
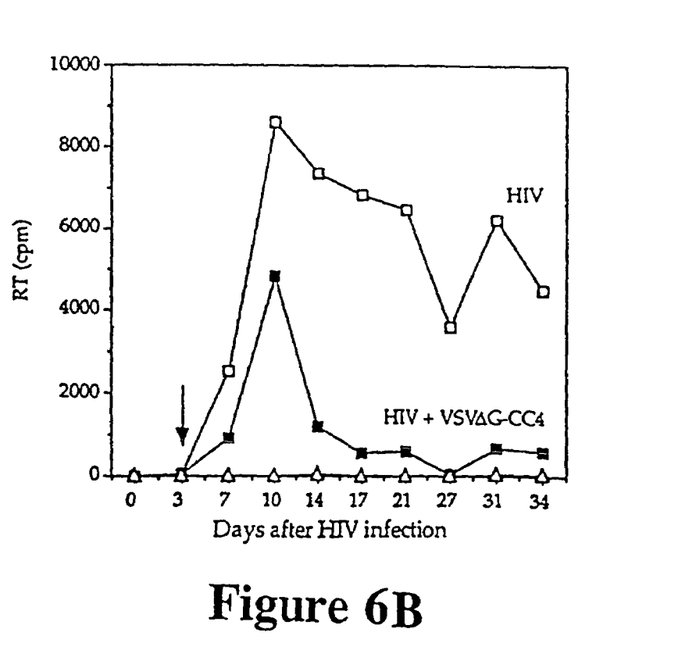

VSVΔG-CC4 infection controls release of infectious HIV-1. To obtain measurements of the effects VSVΔG-CC4 on production of infectious HIV-1 and on release of HIV-1 particles, the experiments shown in FIGS. 4 and 5 were repeated. but instead followed HIV-1 titers and release of reverse transcriptase (RT) into the medium (FIGS. 6A and 6B). At the time of addition of VSVΔG-CC4 at three days after HIV-1 infection, HIV titers and RT levels in the medium were low. In the control cells infected with HIV-1 alone or in the cells super-infected with VSVΔG-CC4, both the HIV titers and RT activity peaked at ten days after infection. There was then a decline in RT activity by day 14 in cells superinfected with VSVΔG-CC4 and a leveling off at about 10% of the RT level seen in control cells. The results with titers of infectious HIV-1 were much more dramatic, with a complete disappearance of infectious HIV-1 (>4 logs below the control) at day 14 followed by a fluctuation at levels of only 0–39 infectious particles per milliliter out to day 34. These titers should be compared to persistent titers of ~$10^4$/ml for the control culture that was not infected with VSVΔG-CC4.

The RT results were consistent with what has been seen previously with the immunofluorescence in FIG. 5, but the much larger decreases in infectious HIV titers were not expected. These lower titers could be explained if the VSVΔG-CC4 infection selected for HIV-infected cells that expressed little or no HIV envelope and thus produced HIV particles lacking envelope but containing RT.

Anti-CD4 or anti-gp120 block infection by VSVΔG-CC4. Control neutralization experiments (Table 1) to verify that entry of VSVΔG-CC4 into HIV infected cells was dependent on CD4 and gp120 were also performed. VSVΔG-CC4 was incubated with antibody to CD4, neutralizing antibody to VSV-G, or without antibody before addition to Jurkat cells that had been infected with HIV-1 for five days as in FIG. 5. Table 1 shows that anti-CD4 completely eliminated the VSVΔG-CC4 infection, while antibody to G did not.

TABLE 1

Neutralization of VSVΔG-CC4 Infectivity

| Antibody[a] | % HIV+ Cells[b] | % VSV N+ Cells[b] |
|---|---|---|
| None | 60 | 39 |
| anti-VSV G | 59 | 37 |
| anti-CD4 | 74 | 0 |
| anti-HIV gp 120 | 71 | 0 |

[a]Viruses grown on BHK cells not expressing VSV G were incubated with anti-VSV G or anti-CD4, or cells were incubated with anti-HIV gp120 prior to mixing of virus and cells.
[b]HIV positive and VSV N+ cells were identified by indirect immunofluorescence microscopy as in FIGS. 4 and 5. Approximately 100 cells from random fields were counted for each determination. The percentage of cells positive for HIV antigens or VSV N protein is indicated.

Similarly, pre-incubation of the HIV-infected cells with a polyclonal anti-gp120 antibody completely prevented infection by VSVΔG-CC4. Because CD4 can bind MHC class II on cell surfaces (Doyle and Strominger, 1987), it was conceivable that some low level of infection could occur after binding of VSVΔG-CC4 to MHC class II on cells, although this would not be expected without a membrane fusion protein. To test this possibility Daudi cells, a lymphocyte cell line known to express abundant quantities of MHC class II protein (Till et al., 1988), was used. These cells were readily infected by wild-type VSV, but no infection by VSVΔG-CC4 was observed.

Discussion

A recombinant VSV that lacks its own envelope protein gene (G) and expresses instead the HIV-1 receptor and coreceptor molecules, CD4 and CXCR4 was constructed. This novel virus is defective for entry into normal cells, but can be propagated on cells expressing a complementing VSV envelope protein. The complemented virus can then be grown on cells not expressing G protein where it buds particles containing CD4 and CXCR4 in the viral membrane. These viruses are replication competent, but can enter and propagate only in cells that are first infected with HIV-1 and express HIV-1 envelope protein. Infection of these cells by VSVΔG-CC4 is neutralized by antibody to CD4 added to the virus, or by antibody to HIV gp120 added to the cells.

The results showed that in a mixed population of cells about half of which were HIV-1-infected and half were uninfected, superinfection with VSVΔG-CC4 ultimately limited production of infectious HIV-1 to levels that were barely detectable or undetectable, at least 300-fold to 104-fold lower than HIV titers produced by control cells that were not superinfected with VSVΔG-CC4. This reduction presumably is the result of killing of the HIV-1 infected cells by the VSVΔG-CC4 virus. The reduction in HIV-1 titers was greater than would have been predicted from analysis of the number of HIV-1-infected cells or from RT assays. The number of HIV positive cells was reduced about ten-fold by the VSVΔG-CC4 infection, and the release of RT was reduced to a similar extent. In considering the mechanism of VSVΔG-CC4 action, this discrepancy is reasonable since VSVΔG-CC4 will target and kill those cells expressing HIV envelope protein and thus select for cells that produce little or no HIV envelope. Such cells would still score positive for HIV-1 antigen production, and would produce normal levels of HIV-like particles containing RT, but the majority of these particles would be noninfectious.

The persistence of a low level of both HIV-1 and VSVΔG-CC4 coinfection for over one month in culture indicates that both viruses are continuing to replicate and that they have reached a balance. Based on the data, it seems unlikely that VSVΔG-CC4 will ever completely eliminate the HIV-1 infection in the culture. This low level persistence may occur because VSVΔG-CC4 can only infect HIV-1 infected cells after gp120/41 is expressed on the cell surface and such cells likely release some HIV-1 before they are killed.

The VSVΔG-CC4 virus infects cells that have already been infected with HIV-1, but it may also be fusing directly with HIV-1 virions. Such fused viruses would contain the nucleocapsids of HIV and VSV and might be able to initiate infection if sufficient gp120/41 were still present on the membrane. Such an infection would almost certainly favor replication of VSVΔG-CC4 because VSV would shut off cellular protein synthesis in 2–3 hours, even before HIV had sufficient time for reverse transcription and integration. Infection by these fused viruses could explain the presence of cells (FIG. 4) that are making VSV proteins but do not appear to have synthesized HIV proteins. While not wishing to be bound to any theory, it is also possible that VSV has inhibited HIV protein synthesis in these cells. Infection of uninfected cells by VSVΔG-CC4 might also occur if VSVΔG-CC4 pseudotypes carrying HIV envelope protein were generated in HIV-infected cells. Incorporation of the wild-type HIV envelope into VSV particles is extremely inefficient (Johnson et al., 1997) and therefore this latter mechanism would likely be rare. To test directly for such pseudotypes, a short-term infection of Jurkat cells with supernatants from cells coinfected with HIV-1 and VSVΔG-CC4 was carried out. VSV protein expression was not detected in these cells, while it was readily detected by using the same supernatant to infect HIV-infected Jurkat cells. It was concluded that the VSVΔG-CC4(HIV) pseudo-types are extremely rare if they exist at all.

Several aspects of this system that are worth noting. First, because VSVΔG-CC4 is specifically targeted to cells already infected with HIV-1, the VSΔG-CC4 infection level would be expected to parallel HIV infection and disappear with clearance of HIV. Second, VSVΔG-CC4 encodes only human proteins as its envelope proteins, and thus would not induce production of neutralizing antibodies. The internal VSV proteins would be expected to induce cytotoxic T cell responses, but such responses might help in clearing HIV infection by rapidly killing cells infected with HIV-1 and VSVΔG-CC4. Third, mutations to drug resistance are rapidly selected in HIV-1, but resistance to infection by VSVΔG-CC4 would require loss of HIV's ability to bind CD4 or corecptor and would therefore not be selected.

The results also illustrate an important aspect of VSV budding and assembly. Based on virus protein yields and titers, it is estimated that each BHK cell infected with wild-type VSV produces approximately 100,000 particles, and up to 10% of these particles are infectious. The deletion of the VSV G gene reduced particle yields of VSVΔG-CC4 or VSVΔG-CD4 approximately 30–50 fold, indicating a substantial role for G in promoting budding. However, despite this reduced budding, at least 2,000 particles of VSVΔG-CC4 or VSVΔG-CD4 are produced from each BHK cell in the absence of G protein. The incorporation of CD4 and CXCR4 into these particles is presumed to occur by a passive process of protein trapping as virus buds from the cell surface, because neither protein would be expected to contain specific signals promoting incorporation. Because VSV blocks host protein synthesis and expresses extremely large amounts of its mRNA and proteins, CD4 and CXCR4 are likely to be the major proteins present on cell surface and therefore the major proteins in the VSVΔG-CC4 envelope.

REFERENCES

Alkhatib, G., Combadiere, C., Broder, C. C., Feng, Y., Kennedy, P. E., Murphy, P. M., and Berger, E. A. (1996). CC CKR5: a RANTES, MIP-1alpha, MIP-1beta receptor as a fusion cofactor for macrophage-tropic HIV-1. Science 272, 1955–8.

Berson, J. F., Long, D., Doranz, B. J., Rucker, J., Jirik, F. R., and Doms, R. W. (1996). A seven-transmembrane domain receptor involved in fusion and entry of T-cell-tropic human immunodeficiency virus type 1 strains. J Virol 70, 6288–95.

Choe, H., Farzan, M., Sun, Y., Sullivan, N., Rollins, B., Ponath, P. D., Wu, L., Mackay, C. R., LaRosa, G., Newman, W., Gerard, N., Gerard, C., and Sodroski, J. (1996). The beta-chemokine receptors CCR3 and CCR5 facilitate infection by primary HIV-1 isolates. Cell 85, 1135–48.

Deng, H., Liu, R., Ellmeier, W., Choe, S., Unutmaz, D., Burkhart, M., Di Marzio, P., Marmon, S., Sutton, R. E., Hill, C. M., Davis, C. B., Peiper, S. C., Schall, T. J., Littman, D. R., and Landau, N. R. (1996). Identification of a major co-receptor for primary isolates of HIV-1. Nature 381, 661–6.

Doranz, B. J., Rucker, J., Yi, Y., Smyth, R. J., Samson, M., Peiper, S. C., Parmentier, M., Collman, R. G., and Doms, R. W. (1996). A dual-tropic primary HIV-1 isolate that uses fusin and the beta-chemokine receptors CKR-5, CKR-3, and CKR-2b as fusion cofactors. Cell 85, 1149–58.

Doyle, C., and Strominger, J. L. (1987). Interaction between CD4 and class II MHC molecules mediates cell adhesion. Nature 330, 256–9.

Dragic, T., Litwin, V., Allaway, G. P., Martin, S. R., Huang, Y., Nagashima, K. A., Cayanan, C., Maddon, P. J., Koup, R. A., Moore, J. P., and Paxton, W. A. (1996). HIV-1 entry into CD4+ cells is mediated by the chemokine receptor CC-CKR-5. Nature 381, 667–73.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872–7.

Florkiewicz, R. Z., and Rose, J. K. (1984). A cell line expressing vesicular stomatitis virus glycoprotein fuses at low pH. Science 225, 721–3.

Fuerst, T. R., Niles, E. G., Studier, F. W., and Moss, B. (1986). Eukaryotic transient-expression system based on recombinant vaccinia virus that synthesizes bacteriophage T7 RNA polymerase. Proc. Natl. Acad. Sci. USA 83, 8122–6.

Johnson, J. E., Schnell, M. J., Buonocore, L., and Rose, J. K. (1997). Specific targeting to CD4+ Cells of recombinant vesicular stomatitis viruses encoding human immunodeficiency virus envelope proteins. J. Virol. 71, 5060–5068.

Knipe, D. M., Baltimore, D., and Lodish, H. F. (1977). Maturation of viral proteins in cells infected with temperature-sensitive mutants of vesicular stomatitis virus. J. Virol. 21, 1149–58.

Lapham, C. K., Ouyang, J., Chandrasekhar, B., Nguyen, N.Y., Dimitrov, D. S., and Golding, H. (1996). Evidence for cell-surface association between fusin and the CD4-gp120 complex in human cell lines. Science 274, 602–5.

Lawson, N. D., Stillman, E. A., Whitt, M. A., and Rose, J. K. (1995). Recombinant vesicular stomatitis viruses from DNA. Proc. Natl. Acad. Sci. USA 92, 4477–81.

Maddon, P. J., Dalgleish, A. G., McDougal, J. S., Clapham, P. R., Weiss, R. A., and Axel, R. (1986). The T4 gene encodes the AIDS virus receptor and is expressed in the immune system and the brain. Cell 47, 333–48.

Mebatsion, T., Konig, M., and Conzelmann, K. K. (1996). Budding of rabies virus particles in the absence of the spike glycoprotein. Cell 84, 941–951.

Moore, J. P. (1997). Coreceptors: implications for HIV pathogenesis and therapy. Science 276, 51–52.

Reed, L. J., and Muench, H. (1938). A Simple Method of Estimating Fifty Percent Endpoints. American Journal of Hygiene 27, 493–497.

Reinherz, E. L., Kung, P. C., Goldstein, G., and Schlossman, S. F. (1979). Separation of functional subsets of human T cells by a monoclonal antibody. Proc. Natl. Acad. Sci. USA 76, 4061–5.

Riedel, H., Kondor-Koch, C., and Garoff, H. (1984). Cell surface expression of fusogenic vesicular stomatitis virus G protein from cloned cDNA. Embo J 3, 1477–83.

Rose, J. K., Buonocore, L., and Whitt, M. A. (1991). A new cationic liposome reagent mediating nearly quantitative transfection of animal cells. Biotechniques 10, 520–5.

Sattentau, Q. J., and Weiss, R. A. (1988). The CD4 antigen: physiological ligand and HIV receptor. Cell 52, 631–3.

Schnell, M. J., Buonocore, L., Kretzschmar, E., Johnson, E., and Rose, J. K. (1996b). Foreign glycoproteins expressed from recombinant vesicular stomatitis viruses are incorporated efficiently into virus particles. Proc. Natl. Acad. Sci. USA 93, 11359–11365.

Schnell, M. J., Buonocore, L., Whitt, M. A., and Rose, J. K. (1996a). The minimal conserved transcription stop-start signal promotes stable expression of a foreign gene in vesicular stomatitis virus. J. Virol. 70, 2318–2323.

Schuitemaker, H., and Miedema, F. (1996). Viral and cellular determinants of HIV-1 replication in macrophages. Aids 10, S25–32.

Shaw, A. S., Amrein, K. E., Hammond, C., Stern, D. F., Sefton, B. M., and Rose, J. K. (1989). The lck tyrosine protein kinase interacts with the cytoplasmic tail of the CD4 glycoprotein through its unique amino-terminal domain. Cell 59, 627–36.

Shockett, P., Difilippantonio, M., Hellman, N., and Schatz, D. G. (1995). A modified tetracycline-regulated system provides autoregulatory, inducible gene expression in cultured cells and transgenic mice. Proc Natl Acad Sci USA 92, 6522–6.

Till, M. A., Ghetie, V., Gregory, T., Patzer, E. J., Porter, J. P., Uhr, J. W., Capon, D. J., and Vitetta, E. S. (1988). HIV-infected cells are killed by rCD4-ricin A chain. Science 242, 1166–8.

Trkola, A., Dragic, T., Arthos, J., Binley, J. M., Olson, W. C., Allaway, G. P., Cheng-Mayer, C., Robinson, J., Maddon, P. J., and Moore, J. P. (1996). CD4-dependent, antibody-sensitive interactions between HIV-1 and its co-receptor CCR-5 [see comments]. Nature 384, 184–7.

Wagner, R. R., and Rose, J. K. (1996). Rhabdoviridae: The viruses and their replication. In Fields Virology, B. N. Fields and D. M. Knipe, eds., (New York: Lippincott-Raven).

Weiss, R. A. (1993). How does HIV cause AIDS? Science 260, 1273–9.

Whelan, S. P. J., Ball, L. A., Barr, J. N., and Wertz, G. T. W. (1995). Efficient recovery of infectious vesicular stomatitis virus entirely from cDNA clones. Proc. Natl. Acad. Sci. USA 92, 8388–8392.

Willey, R. L., Smith, D. H., Lasky, L. A., Theodore, T. S., Earl, P. L., Moss, B., Capon, D. J., and Martin, M. A. (1988). In vitro mutagenesis indentifies a region within the envelope gene of the human immunodeficiency virus that is critical for infectivity. J. Virol. 62, 139–147.

Wu, L., Gerard, N. P., Wyatt, R., Choe, H., Parolin, C., Ruffing, N., Borsetti, A., Cardoso, A. A., Desjardin, E., Newman, W., Gerard, C., and Sodroski, J. (1996). CD4-induced interaction of primary HIV-1 gp120 glycoproteins with the chemokine receptor CCR-5. Nature 384, 179–83.

The papers cited herein are expressly incorporated in their entireties by reference.

The above description is for the purpose of teaching the person of ordinary skill in the art how to practice the present invention, and it is not intended to detail all those obvious modifications and variations of it which will become apparent to the skilled worker upon reading the description. It is intended, how-ever, that all such obvious modifications and variations be included within the scope of the present invention, which is defined by the following claims. The claims are intended to cover the claimed components and steps in any sequence which is effective to meet the objectives there intended, unless the context specifically indicates the contrary.

The invention claimed is:

1. A replication-competent recombinant rhabdovirus whose genome lacks a functional rhabdoviral glycoprotein G gene and encodes at least one foreign polypeptide such that the foreign polypeptide is expressed in the viral envelope of said recombinant rhabdovirus.

2. The recombinant rhabdovirus according to claim 1 wherein the foreign polypeptide is a cellular receptor of another virus which is expressed in the rhabdovirus in a manner sufficient to target cells infected with the other virus.

3. The recombinant rhabdovirus according to claim 1 which is a vesicular stomatitis virus and wherein the foreign polypeptide is a cellular receptor of a pathogenic mammalian virus.

4. The recombinant rhabdovirus according to claim 3 wherein the pathogenic mammalian virus is HIV-1 or HIV-2.

5. The recombinant rhabdovirus according to claim 4 wherein the pathogenic mammalian virus is HIV-1.

6. The recombinant rhabdovirus according to claim 4 wherein the at least one foreign polypeptide is at least one HIV receptor, at least one HIV co-receptor, or mixtures thereof.

7. The recombinant rhabdovirus according to claim 3 wherein the foreign polypeptide is CD4.

8. A replication-competent recombinant vesicular stomatitis virus whose genome lacks a functional vesicular stomatitis virus glycoprotein G gene and which virus encodes at least one HIV receptor and at least one HIV co-receptor such that the HIV receptor and HIV co-receptor are expressed in the viral envelope of said recombinant vesicular stomatitis virus.

9. A recombinant rhabdovirus according to claim 7 whose genome further encodes CXCR4.

* * * * *

UNITED STATES PATENT AND TRADEMARK OFFICE
CERTIFICATE OF CORRECTION

| | | |
|---|---|---|
| PATENT NO. | : 7,081,243 B1 | Page 1 of 1 |
| APPLICATION NO. | : 09/462543 | |
| DATED | : July 25, 2006 | |
| INVENTOR(S) | : Rose et al. | |

It is certified that error appears in the above-identified patent and that said Letters Patent is hereby corrected as shown below:

In the Specification

Column 1, line 8, replace "The invention" with --This invention--;

Column 1, line 8, delete "partial"; and

Column 1, line 9, replace "NIH grants AI24345 and AI49235" with --AI024345, AI049235 and AI030374 awarded by National Institutes of Health--.

Signed and Sealed this
Twenty-third Day of September, 2014

Michelle K. Lee
*Deputy Director of the United States Patent and Trademark Office*

SEQUENCE LISTING

<160> NUMBER OF SEQ ID NOS: 4

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Primer used
      in constructs

<400> SEQUENCE: 1
actgcccggg ctcgaggtta ccatggaggg gatcag                                    36

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Primer used
      in constructs

<400> SEQUENCE: 2
agctgcggcc gctagcttag ctcccgggaa gagatgcg                                  38

<210> SEQ ID NO 3
<211> LENGTH: 41

```
                                   -continued

<212> TYPE: DNA
<213> ORGANISM: Artificial Sequence
<220> FEATURE:
<223> OTHER INFORMATION: Description of Artificial Sequence: Primer used
      in constructs

<400> SEQUENCE: 3
ccgggtacca cgcgtacaat gaaccgggga gtcccttta g                           41

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: Primer used
      in constructs

<400> SEQUENCE: 4
gggcccctcg agcgtgatat ctgttagttt ttttcatact caaatggggc tacatgttct      60
c                                                                     61
```